United States Patent [19]

Schwager

[11] Patent Number: 5,792,075
[45] Date of Patent: Aug. 11, 1998

[54] METHOD AND APPARATUS FOR EXTENDING THE LENGTH OF A GUIDE WIRE

[75] Inventor: Michael Schwager, Winterthur, Switzerland

[73] Assignee: Schneider (Europe) A.G., Bulach, Switzerland

[21] Appl. No.: 832,650

[22] Filed: Apr. 4, 1997

Related U.S. Application Data

[62] Division of Ser. No. 419,779, Apr. 11, 1995, Pat. No. 5,617,875.

[51] Int. Cl.[6] ............................................. A61B 5/00
[52] U.S. Cl. .............................. 600/585; 600/434; 604/280; 604/281
[58] Field of Search .............................. 600/585, 433, 600/434, 435; 604/280, 281, 282

[56] References Cited

U.S. PATENT DOCUMENTS

| | | | |
|---|---|---|---|
| Re. 34,466 | 12/1993 | Taylor et al. | 128/772 |
| 4,003,369 | 1/1977 | Heilman et al. | 128/2 |
| 4,724,846 | 2/1988 | Evans, III | 128/772 |
| 4,779,628 | 10/1988 | Machek | 128/772 |
| 4,827,941 | 5/1989 | Taylor et al. | 128/657 |
| 4,846,193 | 7/1989 | Tremulis et al. | 128/772 |
| 4,854,330 | 8/1989 | Evans, III et al. | 128/772 |
| 4,895,168 | 1/1990 | Machek | 128/772 |
| 4,917,103 | 4/1990 | Gambale et al. | 128/772 |
| 4,958,642 | 9/1990 | Christian et al. | 128/772 |
| 5,031,636 | 7/1991 | Gambale et al. | 128/772 |
| 5,109,867 | 5/1992 | Twyford, Jr. | 128/772 |
| 5,113,872 | 5/1992 | Jahrmarkt et al. | 128/772 |
| 5,127,917 | 7/1992 | Niederhauser et al. | 606/191 |
| 5,139,032 | 8/1992 | Jahrmarkt et al. | 128/772 |
| 5,188,621 | 2/1993 | Samson | 604/283 |
| 5,195,535 | 3/1993 | Shank | 128/772 |
| 5,197,486 | 3/1993 | Frassica | 128/772 |
| 5,217,026 | 6/1993 | Stoy et al. | 128/772 |
| 5,234,002 | 8/1993 | Chan | 128/772 |
| 5,247,942 | 9/1993 | Prather et al. | 128/772 |
| 5,271,415 | 12/1993 | Foerster et al. | 128/772 |
| 5,275,173 | 1/1994 | Samson et al. | 128/772 |
| 5,295,492 | 3/1994 | Sellers | 128/772 |
| 5,339,833 | 8/1994 | Berthiaume et al. | 128/772 |
| 5,361,777 | 11/1994 | Sellers | 128/772 |
| 5,404,886 | 4/1995 | Vance | 128/772 |
| 5,415,178 | 5/1995 | Hsi et al. | 128/772 |
| 5,429,139 | 7/1995 | Sauter | 128/772 |
| 5,441,055 | 8/1995 | Ales et al. | 128/772 |
| 5,497,782 | 3/1996 | Fugoso | 128/772 |
| 5,511,559 | 4/1996 | Vance | 128/772 |
| 5,513,650 | 5/1996 | Johansen | 128/772 |
| 5,527,298 | 6/1996 | Vance et al. | 604/280 |
| 5,546,958 | 8/1996 | Thorud et al. | 128/772 |
| 5,555,893 | 9/1996 | Hackett et al. | 128/772 |
| 5,605,163 | 2/1997 | Hani | 128/772 |
| 5,617,875 | 4/1997 | Schwager | 128/772 |

FOREIGN PATENT DOCUMENTS

| | | |
|---|---|---|
| 0321796A2 | 6/1989 | European Pat. Off. |
| 9218051 | 10/1992 | WIPO |
| 9303664 | 3/1993 | WIPO |

*Primary Examiner*—Max Hindenburg
*Assistant Examiner*—Pamela L. Wingood
*Attorney, Agent, or Firm*—Peter C. Richardson; Lawrence C. Akers; Philip C. Strassburger

[57] ABSTRACT

A docking assembly for the extension of a guidewire. The docking assembly comprises a plug formed at the proximal end of the guidewire, and a socket formed of a tubing permanently bent so as to have a V shaped portion comprised between two straight portions. The end of straight portion is affixed to the distal end of extension wire. A sleeve is slidably engaged over the tubing to substantially straighten it and facilitate insertion of plug into the tubing. Removal of sleeve allows the tubing to recover its preshaped deformation, thereby assuring locking of plug in tubing. To release the assembly it suffices to pull the guidewire and extension wire oppositely to slip the plug out from the tubing.

2 Claims, 4 Drawing Sheets

METHOD AND APPARATUS FOR EXTENDING THE LENGTH OF A GUIDE WIRE

This is a division of application Ser. No. 08/419,779, filed on Apr. 11, 1995, now U.S. Pat. No. 5,617,875.

BACKGROUND OF THE INVENTION

This invention relates to vascular procedures and more particularly to a docking assembly for the extension of a guidewire with an extension wire, comprising plug means and socket means, in which the plug means are releasably held in the socket means.

It is common practice to use a guidewire for the placement of a catheter in vascular procedures such as angioplasty. A guidewire typically is slightly longer than the catheter with which it is used, whereby a relatively short portion of the guidewire protrudes proximally form the catheter when the catheter is in place. If it becomes necessary to exchange the catheter, for instance to increase the balloon size in an angioplasty procedure, the guidewire must be removed and replaced by an exchange wire which is about twice the length of the catheter in order to allow withdrawal of the catheter and insertion of a new catheter over the exchange wire. However, this technology seriously complicates and slows down the vascular procedure, and there has been several attempts to attach an extension wire to the initial guidewire in order to eliminate the need of a separate exchange wire.

The document EP 0321796 A2 describes an extendable guidewire system comprising a main guidewire section and a guidewire extension section and a connection therebetween including a tubular member fixed to the end of one of the guidewire sections and a male member arranged on the end of the other guidewire section which has a maximum radial dimension which is greater than the inner diameter of the tubular member, whereby the male member may be inserted into the tubular member to releasably secure to two guidewire sections together.

According to a first embodiment, the male member is shaped into an undulating or sinusoidal shape. According to a second embodiment, the male member is provided with a smaller diameter portion having radial protrusions.

Hence, deformation of the undulating shape of the male member provides for a friction fit of the male member into the tubular member and the two guidewire sections may be connected or disconnected as desired. The need of radial deformation of the preshaped male member to generate the friction fit requires a distinct difference in diameter between the inner diameter of the tubular member and that of the male member. Therefore, the male member has to be extremely thin and it may be easily bent inadvertently, thereby spoiling the guidewire section to which it belongs. Furthermore, as the insertion of the male member into the tubular member is made against friction forces, these forces may cause buckling, and even total kinking of the male member with sinusoidal shape, also spoiling the corresponding guidewire section. In case of the male member with radial protrusions the male member is straight and will shown less tendency to buckling and kinking upon insertion by the male member then is very difficult to manufacture. No special tool or pliers are used in this system to form the lock by the user, however the system relies entirely on friction forces. Upon contact with body fluids or medication fluids the friction surfaces may become slippery so that the required friction forces are no longer available.

U.S. Pat. No. 4,917,103 shows a guidewire system in which a steel tubular connector is attached to the proximal end of a guidewire and a reduced diameter steel tip is attached to the distal end of an extension wire.

The contrary is also possible, with the tubular connector on the extension wire and the reduced diameter tip on the guidewire. For connecting the extension wire to the guidewire, the reduced diameter tip is inserted into the tubular connector and the assembly of both the tip and connector is crimped by means of appropriate pliers used as a crimping tool. Mechanical attachment of both parts is thus obtained by displacing a segment of both the tubular connector and tip inserted therein laterally of their general axis in what may be considered as a generally U-shaped configuration. The extent of lateral displacement is of course selected so that it will not interfere too much with the smooth advancement of a catheter over the point of assembly. To release or disconnect the assembly of guidewire and extension wire, it is necessary to cut the guidewire distally of the crimp or to break the connection at the location of the crimped tubular connector and tip assembly.

The system is thus a permanent connection, and when released by cutting the guidewire or breaking the connector and tip assembly, both the guidewire and extension wire are spoiled, which makes it that the system is definitely not re-usable. In addition, the cutting-out of the guidewire or the breaking of the connector and tip assembly may prove difficult or even impossible without some special cutting tool. And this adds to the fact that the need to use a crimping tool for the mechanical attachment of the tubular connector and tip renders the system dependent from the proper use of the crimping tool. This system has the advantage that it has no preshaped male member that may be buckled or a male member with protrusions that are difficult to manufacture. It has also the advantage that it does not rely entirely on friction forces which makes this system more independent from potential wetting influences by body fluids or by medical fluids, however this system has the drawback that the extension can only be made with the help of some additional tool.

It is an object of this invention to improve the possibilities of attaching an extension wire to a guidewire and to avoid the aforesaid drawbacks. It is a further object of the invention to achieve attachment and release of a guidewire and extension wire by means of a docking assembly which is simple, inexpensive and easy to manufacture, which guarantees a smooth, effortless, efficient and repetitive operation for both connection and release of the guidewire and extension wire, which does not require skills or tooling manipulations, and which is still releasably licking even after being wetted with slippery fluids.

SUMMARY OF THE INVENTION

Docking in the present invention is simply achieved by insertion of the plug means into the somewhat straightened socket means and thereafter release of the socket means so that they may return to their preshpaed permanent lateral deformation. By this deformation, the plug means are bent into a deformation substantially corresponding to that of the socket means being thereby secured inside the socket means.

To release the assembly, the plug means may be withdrawn from the socket means by just pulling them out. The pulling forces stretch the deformation in the connection and the plug means may slip out of the socket means.

The docking and release of the assembly may be repeated at will. As the forces necessary for insertion of the plug means into the socket means are smaller than the locking forces, an easy feed and strong lock is achieved without risk for the plug means which may be extremely thin. As the assembly is determined by integers which are not dependent on dimensions delimited by the guidewire diameters, there are no tolerance problems or delicate shapes to master in the manufacture of the functional elements of the assembly, whatever the limits of the confined space delimited by the diameter of the guidewire.

When the socket means are preshaped in the lateral deformation no crimping tool is necessary to form the lateral deformation for docking.

When the element with a preshaped laterally deformed longitudinal axis is formed by the socket means, the preshaped element because of its natural hollow structure shows more inherent rigidity than the plug means. At the same time the plug can be straight, so that the plug shows no points of discontinuance which may be either difficult to manufacture or which cause buckling upon insertion of the plug.

If the locking of the assembly is achieved by a common lateral deformation of both the plug means axis and the socket means axis, then the locking assembly does not rely entirely on friction forces which might be disturbed by body fluids or medication fluids.

An easy way to facilitate straightening of the socket means is to make use of a sleeve slipped over the socket means. A further way to facilitate straightening of the socket means is to make use of a sleeve slipped over the socket means, which sleeve has a longitudinal groove for taking up the socket means and surface means inserted into said groove for pressing the socket means into the groove.

In sum, the present invention relates to a guidewire attachment assembly having a) an essentially straight elongated member; and b) a resilient tubular member preshaped in a non-straight configuration and adapted to assume a straighter configuration upon an application of force thereto; wherein the resilient tubular member is adapted to receive the elongated member while the resilient tubular member is in the straighter configuration. The resilient tubular member may be adapted to assume a straighter configuration upon the application of internal force therein and/or external force thereon.

In another embodiment, the invention relates to a guide wire attachment assembly comprising: a) a resilient elongated member preshaped in a non-straight configuration and adapted to assume a straighter configuration upon an application of force thereto; and b) a tubular member; wherein the tubular member is adapted to receive the resilient elongated member while the resilient elongated member is in the straighter configuration. The resilient elongated member may be adapted to assume a straighter configuration upon the application of internal force therein and/or external force thereon.

In another embodiment the invention relates to a guidewire attachment assembly comprising: a) a resilient elongated member preshaped in a first non-straight configuration and adapted to assume a first straighter configuration upon an application of force thereon; and b) a resilient tubular member preshaped in a second non-straight configuration and adapted to assume a second straighter configuration upon an application of force thereon; wherein the resilient tubular member, while it is in the second straighter configuration, is adapted to receive the resilient elongated member, while it is in the first straighter position. The resilient elongated member and/or the resilient tubular member may be adapted to assume straighter configuration upon the application of internal force therein and/or external force thereon.

The present invention also relates to a docking assembly for the extension of a guidewire with an extension wire, having plug means and socket means, in which the plug means are held in the socket means, by a common lateral deformation of the plug means and the socket means, wherein the socket means are preshaped in the lateral deformation. The plug means may have a longitudinal axis and socket means may also have a longitudinal axis, in which the plug means are held in the socket means by lateral deformation, in which the plug means and the socket means represent elements of the docking system and in which one element of the docking assembly has a preshaped laterally deformed longitudinal axis, wherein the element with a preshaped laterally deformed longitudinal axis is formed by the socket means. In another embodiment, the docking assembly for the extension of a guidewire with an extension wire has plug means having a longitudinal axis and socket means also having a longitudinal axis, in which the plug means are held in the socket means by lateral deformation, in which the plug means and the socket means represent elements of the docking system and in which one element of the docking assembly has a preshaped laterally deformed longitudinal axis, wherein that the locking of the assembly, is achieved by a common lateral deformation of both, the plug means axis and the socket means axis. The socket means may be substantially contoured according to a V shape, or a contoured portion between two straight portions. The docking assembly may further comprise sleeve means for substantially straightening the socket means, which may be slidably engaged over the socket means. The sleeve means may comprise groove means for taking up the socket means and surface means inserted into said groove means for pressing the socket means into said groove means. The common lateral deformation of both the plug means axis and the socket means axis may be non permanent. The socket means may be made of an elastic Nickel Titanium alloy.

BRIEF DESCRIPTION OF THE DRAWINGS

These and other features of the invention will be appreciated more fully from the following further description thereof, with reference to the accompanying diagrammatically exemplary drawings in which.

DESCRIPTION OF THE PREFERRED EMBODIMENT

Figure 1:
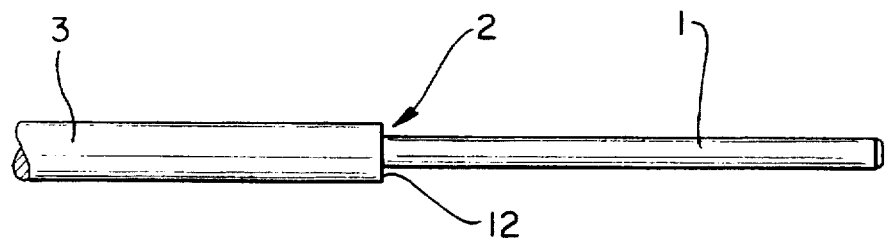
FIG. 1 is a longitudinal view of the plug means.

The plug means shown in FIG. 1 are made of a portion 1 ground along the longitudinal axis of the proximal end 2 of the guidewire 3.

Figure 2:
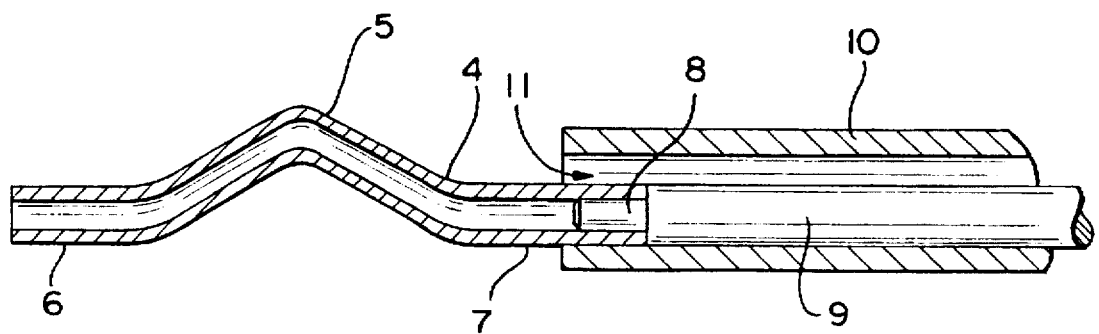
FIG. 2 is a longitudinal view of the socket means.

The socket means shown in FIG. 2 comprise a tubing 4 permanently bent along its longitudinal axis so as to have a V portion 5 comprised between two straight portions 6 and 7, the socket means being thus preshaped in a lateral deformation. The end of straight portion 6 is free while the end of straight portion 7 is engaged and affixed, for instance bonded, to a tip portion 8 ground at the distal end of extension wire 9.

The tubing 4 is preferably made of a highly elastic Nickel Titanium alloy such as for instance Nitinol (tradename) which has the advantage of an increased elasticity allowing large deformations without causing a permanent deformation; a further advantage of such a material is that the tubing does not increase the rigidity of the extension wire in the docking area.

However, other materials may also be used, inasmuch as they provide acceptable biocompatibilty.

A sleeve 10 is engaged over the distal end of extension wire 9. This sleeve is adapted to be slipped over the tubing 4 and its lumen 11 has a diameter such that the sleeve substantially straightens the V portion 5 of the tubing 4 when slipped thereover, as shown in FIG. 3.

Figure 3:
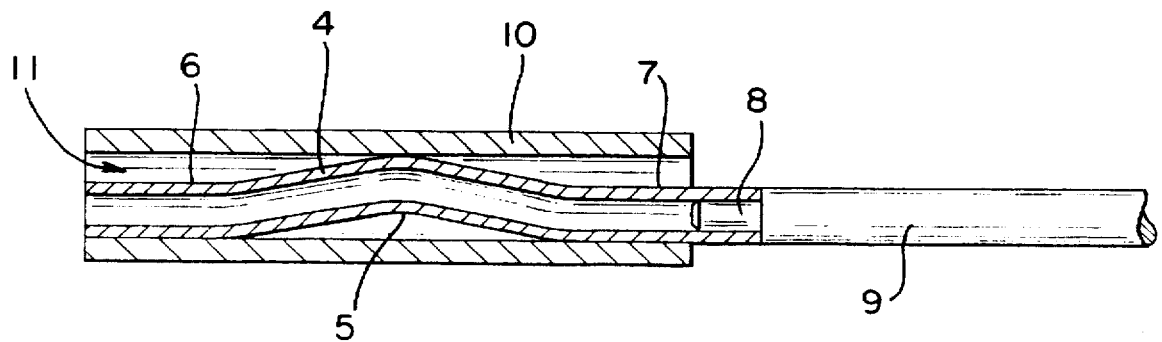
FIGS. 3, 4 and 5 are longitudinal sectional views showing assembly of the elements shown in FIGS. 1 and 2.
Figure 4:
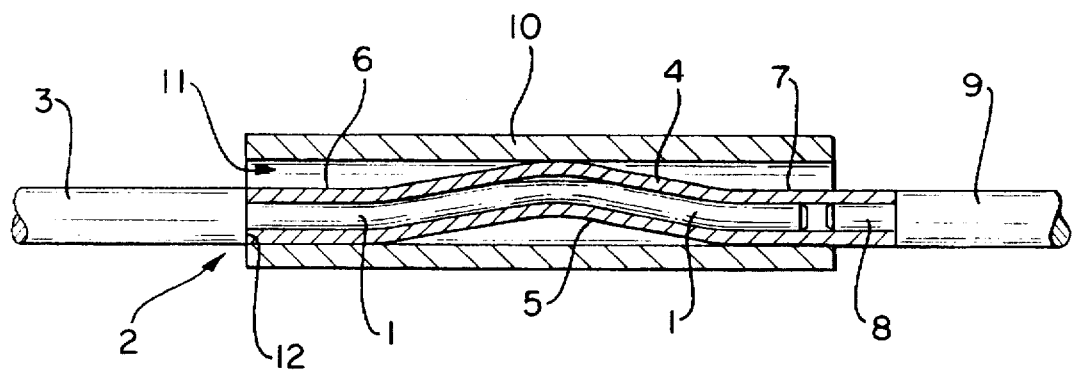
Figure 5:
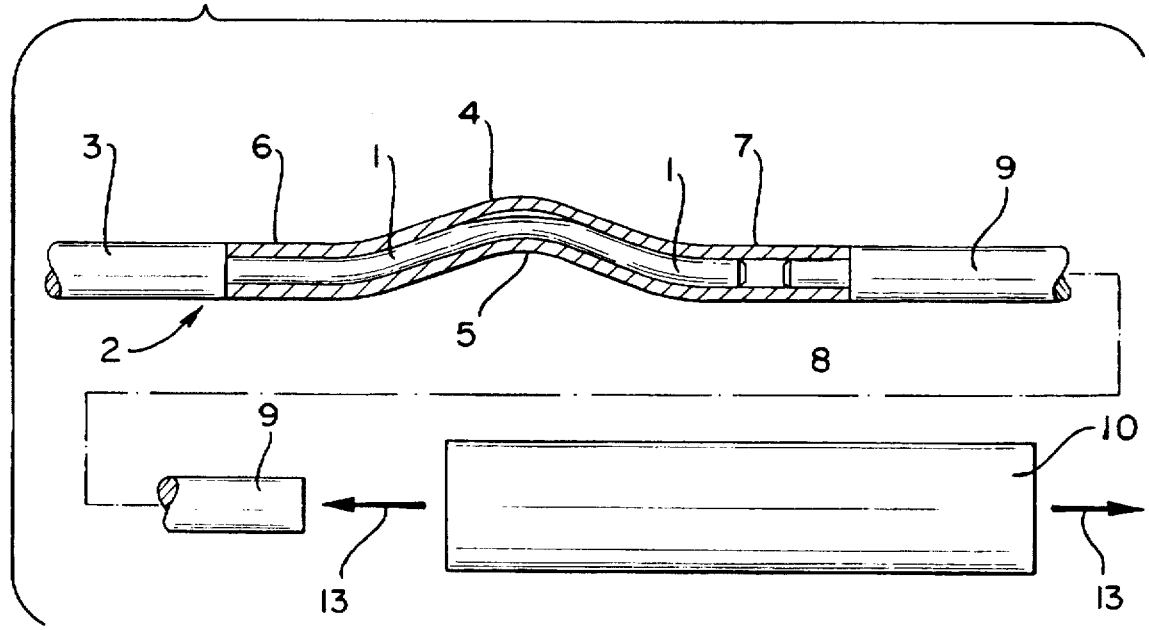

FIGS. 3, 4 and 5 illustrate the assembly and release of the plug means (1) and socket means (4) which represent elements of a docking system in which one element of the docking assembly has a preshaped laterally deformed longitudinal axis, wherein the element with a preshaped laterally deformed longitudinal axis is formed by the socket means (4).

Initially, the extension wire 9 is preferably made available with the sleeve 10 slipped over the tubing 4 in order to present its V portion 5 in a substantially straight configuration, as shown in FIG. 3.

When extension of the guidewire 3 is needed, the ground portion 1 of the proximal end of the guidewire 3 is inserted into the straight portion 6 of tubing 4 and pushed therein. When arriving at the substantially straightened V portion 5 of tubing 4, the ground portion 1 is further pushed therein and its flexibility allows its following the substantially straight contour of the portion 5 of tubing 4. After reaching the end of portion 5 of tubing 4, the ground portion 1 is further pushed to reach straight portion 7 of tubing 4, at which time the junction 12 of ground portion 1 to the full end 2 of guidewire 3 abuts against the free end of straight portion 6 of tubing 4.

At that time, it suffices to slip the sleeve 10 towards the proximal end of extension wire 9 and to remove it therefrom as shown by arrows 13 in FIG. 5.

Upon movement apart of the sleeve 10, the substantially straightened portion 5 of tubing 4 is no more under the constraint of lumen 11 of the sleeve 10, and the portion 4 recovers by intrinsic elasticity its permanently preshaped lateral deformation as illustrated in FIG. 5. Due to its flexibility, the ground portion 1 of guidewire 3 is bent correspondingly and substantially follows the lateral deformation of tubing 4, being thus firmly secured inside the tubing 4. The locking assembly is therefore achieved by a common lateral deformation of both the plug means axis and the socket means axis. Depending on the choice of materials, this common lateral deformation will be non permanent.

To release the assembly, it suffices to pull the guidewire and extension wire oppositely, which causes the ground tip 1 to withdraw from tubing 4. Once the ground tip is fully withdrawn, the tubing 4 recovers its fully bent V configuration at portion 5 as illustrated in FIG. 2.

The whole operation may be repeated at will. It suffices to re-engage sleeve 10 on the proximal end of extension wire 9 and to slip it over the tubing 4. Engagement of sleeve 10 on the distal end of extension wire 9 is also possible, being sufficient to engage the sleeve 10 over the straight portion 6 of tubing 4 and thereafter to push it towards the straight portion 7, thereby substantially straitening the V portion 5 of the tubing.

Figure 6:
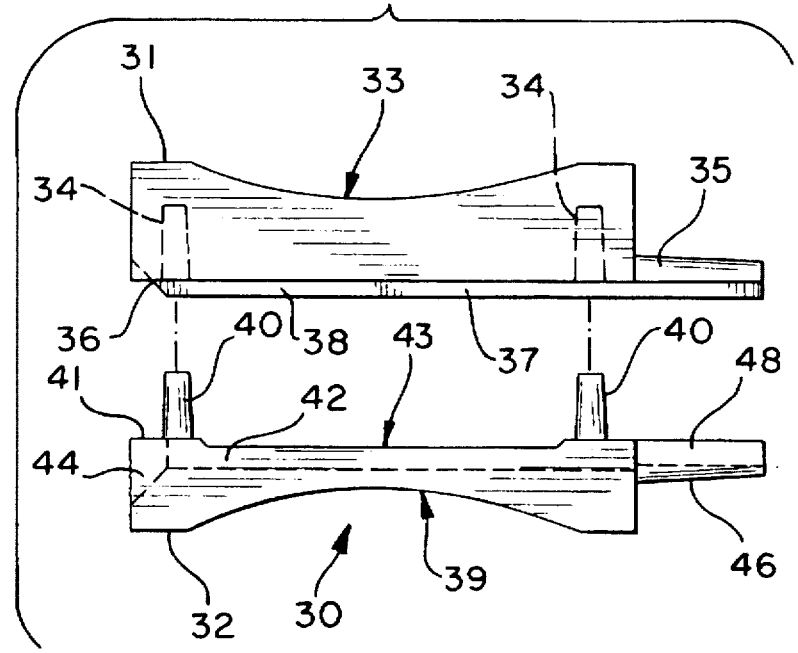
FIGS. 6 and 7 are longitudinal and end views of the elements forming a sleeve used for the assembly of the plug means and socket means.
Figure 7:
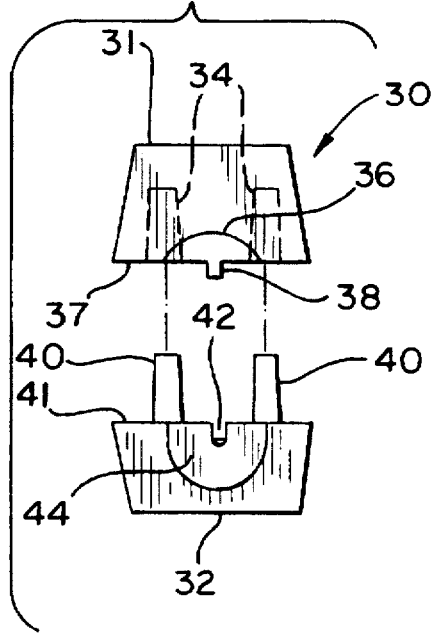
Figure 8:
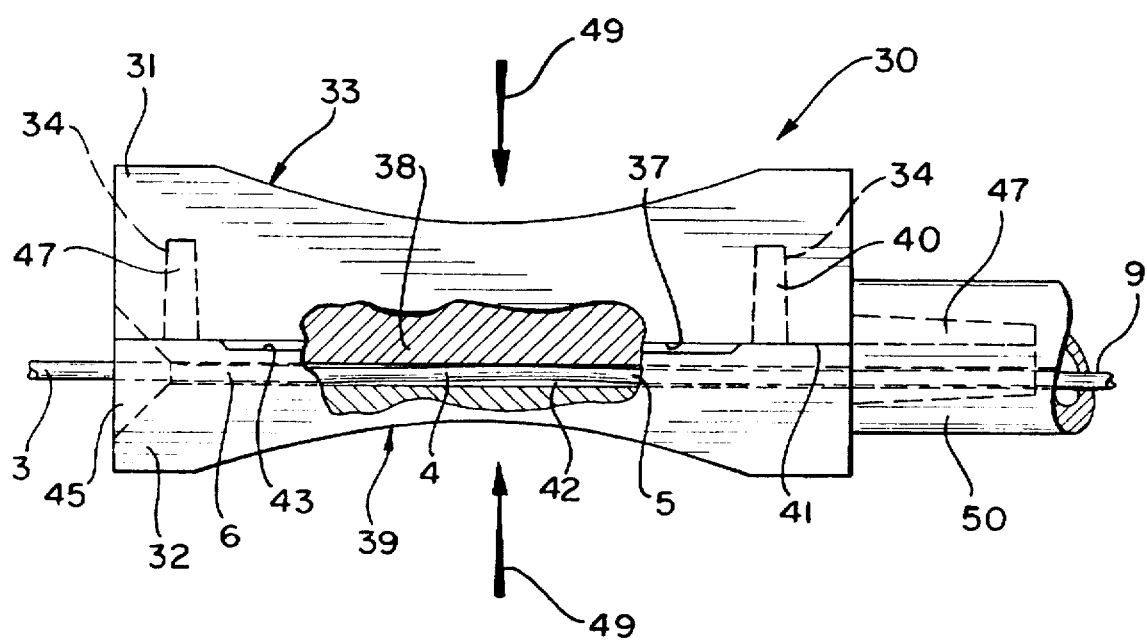
FIG. 8 is a longitudinal partly sectional view showing assembly of the elements shown in FIGS. 6 and 7.

The sleeve 10 may be replaced by a sleeve 30 as exemplified in FIGS. 6, 7 and 8. Sleeve 30 is formed of two shells 31 and 32 adapted to fit to one another.

Shell 31 comprises an arcuate finger rest 33 and positioning recesses 34. Opposite to finger rest 33, the shell comprises a flat wall 37 and a longitudinal edge 38 extending perpendicularly of the flat wall 37.

Left hand side end of shell 31 is provided with a conically shaped recess 36; right hand side end of shell 31 is provided with a semi-conical plug 35 extending over the longitudinal edge 38.

Shell 32 comprises an arcuate finger rest 39 and studs 40 adapted to fit into the positioning recesses 34 of shell 31. Opposite to finger rest 39, the shell 32 comprises a flat wall 41 and a longitudinal groove 42 extending perpendicularly of the flat wall 41 and intended to house longitudinal edge 38 of shell 31. Over some length between the studs 40 the flat wall 41 comprises a depression 43 adapted to face flat wall 37 of shell 31. Left hand side end of shell 32 is provided with a conically shaped recess 44 adapted to form with recess 36 of shell 31 a conical recess 45 surrounding the corresponding extremity of groove 42; right hand side end of shell 32 is provided with a semi-conical plug 46 which is intended to form a conical plug 47 with semi-conical plug 35 of shell 31. Semi-conical plug 46 contains a longitudinal groove 48 extending from longitudinal groove 42, groove 48 being however less deep than groove 42.

FIG. 8 illustrates the assembly of the shells 31 and 32 shown in FIGS. 6 and 7, with studs 40 inserted into recesses 34 and flat wall 37 facing flat wall 41 and depression 43, with semi-conical recesses 36 and 44 forming conical recess 45 and semi-conical plugs 35 and 46 forming conical plug 47, and with longitudinal edge 38 inserted into longitudinal grooves 42 and 48.

As in the case of sleeve 10, the extension wire 9 will be preferably made available with the sleeve 30 slipped over the tubing 4 in order to present its V portion 5 in a substantially straight configuration as shown in FIG. 8; a tube 50 for packaging extension wire 9 may have its distal end force fitted over conical plug 47 to help holding shells 31 and 32 applied against each other in addition to protecting the extension wire.

When extension of the guidewire 3 is needed, the operator takes the sleeve 30 and squeezes it by exerting finger pressure over finger rests 33 and 39 in the direction of arrows 49; such a pressure causes flat wall 37 of shell 31 to somewhat bend into depression 43 of flat wall 41 of shell 32, thereby urging the longitudinal edge 38 into longitudinal grooves 42 and 48 of shell 32, whereby V portion 5 of tubing 4 will be still more straightened by the pressure of the lower surface of longitudinal edge 38 while the distal end of the extension wire 9 will be firmly held by the extremity of longitudinal edge 38 penetrating into groove 48.

The plug means of the proximal end of the guidewire 3 may then be inserted into the straight portion 6 of tubing 4 and pushed therein. Conical recess 45 facilitates location of the plug means into the entry of the tubing 4. As in the case of the sleeve 10, the plug means are pushed fully through the socket means, which operation is greatly facilitated by the extra straightening of tubing 4 afforded by the pressure of the lower surface of longitudinal edge 38.

At that time, it suffices to release the finger pressure exerted on finger rests 33 and 39 and to slip the sleeve 30 towards the proximal end of extension wire 9 to relieve the constraints exerted on tubing 4 which will recover its permanently preshaped lateral deformation, thereby firmly securing the plug means into the socket means. To release the assembly, it suffices to pull the guidewire and extension wire oppositely as previously explained, and the whole operation may also be repeated at will.

Variants may be envisaged.

The plug means may be formed of a thin tubing portion affixed to the proximal end of the guidewire instead of the ground portion 1 as described.

Instead of having the plug means on the proximal end of the guidewire and the socket means on the distal end of the extension wire, as shown in FIGS. 1 to 5, it would be possible to do the opposite. The solution shown is however preferred because it permits to have the extension wire ready as a fully equipped additional unit while leaving the proximal end of the guidewire free of elements which might trouble the practitioner.

It is possible to avoid usage of sleeves 10 or 30, the straightening of the tubing 4 being made by hand squeeze for insertion of the ground portion 1 into the tubing 4.

The tubing 4 may be permanently bent according to a shape different from the V contour shown in FIGS. 2 to 5. For instance, a sinusoidal shape may also be used, with straight proximal and distal portions as shown for the V shaped bent portion 5.

Of course, whatever the permanently bent socket means used, the length of the plug means or ground portion 1 will have to be selected in such a way that the plug means sufficiently penetrate the permanently bend socket means in order to assure the required attachment of these two parts.

Similarly, the plug means may be affixed to the corresponding element, guidewire or extension wire, by bonding or otherwise, instead of being ground in the corresponding element. That would allow selecting for the plug means a material other than that of the element to which they correspond.

The foregoing description, and the accompanying figures, are presented for the purpose of illustrating, and not limiting, the present invention.

I claim:

1. An assembly for extending the length of a guidewire, the assembly comprising:
   (a) essentially straight elongated means;
   (b) resilient tubular means preshaped in a non-straight configuration; and
   (c) sleeve means adapted for placement about the resilient tubular means for forcing the resilient tubular means into a straighter configuration;
   wherein the resilient tubular means is adapted to receive the elongated means while the resilient tubular means is in the straighter configuration.

2. A method of extending the length of a guidewire, the method comprising:
   (a) providing an assembly comprising essentially straight elongated means; resilient tubular means preshaped in a non-straight configuration; and sleeve means adapted for placement about the resilient tubular means for forcing the resilient tubular means into a straighter configuration; wherein the resilient tubular means is adapted to receive the elongated means while the resilient tubular means is in the straighter configuration;
   (b) disposing the sleeve means about the resilient tubular means to force the resilient tubular means into a straighter configuration;
   (c) inserting the essentially straight elongated means into the resilient tubular means while the resilient tubular means is in the straighter configuration; and
   (d) removing the sleeve means from the resilient tubular means while the essentially straight elongated means is inserted therein, thereby allowing the resilient tubular means to return at least partially to the non-straight configuration.

* * * * *